United States Patent [19]

Dawes et al.

[11] 4,118,367

[45] Oct. 3, 1978

[54] REINFORCED RUBBER

[75] Inventors: Keith Dawes; Roger James Rowley, both of London, England

[73] Assignee: The Malaysian Rubber Producers Research Association, England

[21] Appl. No.: 763,117

[22] Filed: Jan. 27, 1977

[30] Foreign Application Priority Data

Feb. 6, 1976 [GB] United Kingdom ............... 4802/76

[51] Int. Cl.$^2$ ............................................. C08K 5/54
[52] U.S. Cl. ............................. 260/42.37; 260/42.15; 260/42.44; 260/192; 260/756
[58] Field of Search ................. 260/192, 42.15, 42.37, 260/42.44, 756

[56] References Cited

U.S. PATENT DOCUMENTS 3,768,537  10/1973  Hess et al. ......................... 260/42.37
3,778,430  12/1973  Citron et al. ........................ 260/192

Primary Examiner—James H. Derrington
Attorney, Agent, or Firm—Wenderoth, Lind & Ponack

[57] ABSTRACT

The invention relates to the production of silica reinforced rubber incorporating a novel azo-silane coupling agent which does not depend on the vulcanization reaction to effect coupling to the rubber. The novel coupling agents are of the general formula:

$$Y - X - CO - N = N - CO - X^1 - Z$$

where X and $X^1$ are the same or different and each is an imino group, an oxygen atom, or a substituted or unsubstituted methylene group; Y is a substituted or unsubstituted alkyl, aryl or aralkyl group or is the same as Z; and Z as an alkyl, aryl or aralkyl group which has an substituent at least one silane group of the formula: $-Si(OR)_3$ or $-OSi(OR)_3$ in which R is a straight or branched chain alkyl group. The azo-silane is typically used in amounts of from .1 to 10 pphr. Silica reinforced rubber vulcanizates produced using the azo-silane can have improved properties e.g. abrasion resistance, scorch resistance and resilience as compared with vulcanizates made using conventional coupling agents.

15 Claims, No Drawings

REINFORCED RUBBER

This invention relates to novel chemical compounds and to their use in rubber which is reinforced with silica.

For applications requiring high strength and abrasion resistance, particularly such as tyres and conveyor belting, rubber articles contain substantial amounts of reinforcing fillers. Carbon black is one effective reinforcing filler and is widely used but although giving excellent physical properties suffers from the disadvantage that the articles are always black in colour because of the heavy pigmenting effect. The use of silica, silicates and clays as an alternative has been common for many years, but has presented difficulties in practice, since the tensile strength and abrasion resistance are lower than for corresponding carbon black-filled vulcanizates.

These difficulties have been ascribed by some workers to the lack of physical or chemical bonding between the silica particles and the rubber molecules, and various treatments have been devised to overcome them. The silica may be subjected to a heat treatment to activate its surface, or it may be treated with chemicals to modify the surface and provide bonding sites for the rubber molecules. Alternatively, reagents capable of reacting both with the silica surface and the rubber molecule, known in the art as coupling agents, may be added to the rubber mix during the processing stage.

The coupling agents and surface modification agents generally consist of a silane which has a substituent group capable of reacting with the rubber molecule. The silane forms a bond to the silica surface, probably through hydrolysis, and the rubber reactive group combines with the rubber molecule during vulcanization. The reactive groups used include mercapto, amino, vinyl, epoxy, methacrylo, glycidoxy and amyl groups, the mercapto and amino groups being the most effective. However, these groups are similar to those involved in the normal vulcanization process, and interference between the two reactions occurs, giving rise to problems of low scorch safety.

We have now found that certain classes of substituted azo compounds can provide a silane coupling agent with a reactive group which will react readily and substantially quantitatively with the rubber independently of the vulcanization reaction. It therefore becomes possible to complete the reinforcing process before vulcanization, and to obtain a controlled amount of reinforcement without impairing the normal vulcanization process. A further advantage is that the dispersion of the reinforcing agent can be improved.

The invention accordingly provides compounds of the general formula I:

$$Y - X - CO - N = N - CO - X^1 - Z \qquad (I)$$

where

X and $X^1$ are the same or different and each is an imino group, an oxygen atom or a substituted or unsubstituted methylene group;

Y is a substituted or unsubstituted alkyl, aryl or aralkyl group, or is the same as Z; and Z is an alkyl, aryl or aralkyl group which has as substituent at least one silane group of the formula: Si(OR)$_3$ or OSi(OR)$_3$ in which R is a straight or branched chain alkyl group, preferably with 1 to 6 carbon atoms.

Azo compounds are known to react with unsaturated organic compounds via the 'ene' reaction (H. M. R. Hoffman, Angew, Chem. Internat. Edn, 1969, 8, 556). The reaction of some cyclic 4-substituted-1,2,4-triazoline-3,5-diones with unsaturated elastomers is described in U.S. Pat. No. 3,966,530.

It will be appreciated that the nature of the group Y in formula I will have only a slight effect on the reactivity of the azo compound towards the unsaturated rubber molecule, and the precise nature of the alkyl, aryl or aralkyl group is not critical provided it does not prevent the reaction from taking place. In the same way the nature of the group R in the silane group is critical insofar as it may prevent reaction between the silane group and the silica. Especially suitable for the invention are compounds of the general formulae II and III:

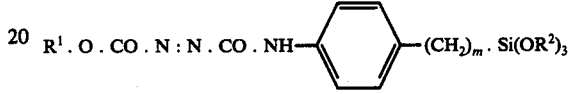

$$R^1 . O . CO . N : N . CO . NH . (CH_2)_n . Si(OR^2)_3 \qquad (III)$$

where $R^1$ and $R^2$ are the same or different and each is a straight or branched chain alkyl group preferably containing from 1 to 6 carbon atoms, $m$ is 0, 1, 2 or 3 and $n$ is 1, 2 or 3.

Compounds of formulae II and III and compounds of formula I generally can be made by oxidation of the corresponding hydrazo compounds. The oxidation takes place readily by the methods known for analogous hydrazo compounds, the reaction with N-bromosuccinimide being particularly convenient. Suitable hydrazo compounds may be obtained by the reaction of a substituted carbazate with a substituted isocyanate. Thus hydrazo compounds corresponding to the general formula II may be made by condensing an alkyl ($R^1$) carbazate with a p-isocyanato-aryl or p-isocyanatoaralkyl tri-($R^2$)-alkoxy silane.

Similarly, hydrazo compounds corresponding to the general formula III may be made by condensing an alkyl ($R^1$) carbazate with an isocyanato-alkyl tri-($R^2$)-alkoxysilane. The required isocyanato-trialkoxysilane may often be prepared advantageously by treating the corresponding amino-trialkoxy-silane with ethyl or phenyl chloroformate to give the carbamate which is then converted to its trimethylsilyl derivative and pyrolysed.

The main utility of the azosilane compounds of the present invention envisaged is as treating agents to improve the compatibility of silica, silicates and clays when compounded in rubber. For convenience reference to silica as a reinforcing material herein is to be understood as including silicates and clays such as are conventionally used to reinforce rubber. The invention accordingly includes a method of compounding rubber with silica which comprises including in the rubber a compound of the invention. The method of the invention is applicable to natural rubber and to unsaturated synthetic rubber. The silica conventionally used in compounding rubbers is a chemically derived product obtained by precipitation from solution. The silicates and clays can be either natural or synthetic products.

Within the method of the invention there are two subsidiary methods which merit specific mention as each has particular application. They may be summarised as follows:

1. Pre-treatment of the rubber with an azosilane of the invention.
2. Adding an azosilane of the invention during compounding.

Thus in a first subsidiary aspect the invention provides a method of treating rubber prior to compounding with silica, which method comprises adding to the rubber a compound of the invention. In this aspect, the rubber may be treated in the form of solid rubber or rubber solution. The azosilane can be incorporated into the rubber as liquid 100% compound, or, especially for treating rubber solution, in solution in an organic solvent. In the treated rubber the azosilane reacts with the rubber to produce a modified rubber. The modification reaction proceeds readily at moderately elevated temperatures, but will also occur at a rather slower rate, at ambient temperatures. For the useful range of concentrations of the azosilane, typical periods for completion of reaction are about 24 hours at 20° C. and about 2 minutes at 100° C. Thus, where the treated rubber is stored before compounding with silica, it will not normally be necessary to heat the treated rubber before compounding it. However where the rubber is used very soon after treatment, then it is preferable to heat the treated rubber to ensure completion of the modification reaction. The heating temperature preferably should not exceed 100° C. because at higher temperatures undesired side reactions can occur reducing the number of sites available for bonding to the silica.

In the case of dry rubber the azosilane may be added on a mill or in an internal mixer, when the reaction may take place partly or completely during mixing. It is best to add the reagent on a cool mill, preferably at 50° C. to 100° C., to ensure adequate dispersion before the reaction takes place to any appreciable extent. The rubber may then be heated if necessary to complete the reaction or allowed to cool and stand for a suitable period at room temperature e.g. overnight.

Where the rubber is being treated in solution, the azosilane can be added with stirring in a suitable organic solvent. The mixture can then be stored or heated to complete reaction and the modified rubber recovered by precipitation from the solution or evaporation of the solvent. Alternatively the treated rubber can be recovered by evaporation of the solvent and the modification reaction completed subsequently.

In the second subsidiary aspect the invention includes a method of making a silica compounded rubber which method comprises compounding silica into rubber and mixing into the rubber or compounded rubber, immediately before, during or after compounding, an azosilane of the invention. This aspect of the invention specifically relates to where the rubber is compounded before the azosilane has reacted with either rubber or silica and includes adding the azosilane after the silica has been compounded into the rubber. The reaction of the azosilane with the rubber can be completed either by storing the compounded rubber or more preferably by heating the compounded rubber which may, and usually will, include other compounding ingredients including vulcanizing agents and accelerators. It is a particular advantage that the reaction of the azosilane with the rubber can be carried out rapidly at temperatures below those at which the rubber vulcanizes thus avoiding interference between the modification and vulcanization reactions.

With regard to the preferred compounds of the invention, compounds of the formula II may undergo some decomposition if subjected to temperatures above about 100° C. and it may be preferable to add such compounds on a mill after the silica has been compounded with the rubber. However, compounds of the formula III have the advantage that they are less susceptible to decomposition by heat and may be subjected to temperatures of up to about 150° C. without undergoing substantial decomposition. They can therefore often be added in the internal mixer before, with or after the silica.

The reaction of the azosilane with the silica readily occurs at the temperatures of normal vulcanization procedures. Thus does not seem to be a problem, since the reaction of the silane groups with the silica does not appear to seriously interfere with vulcanization. As has been mentioned above, it is possible and may be desirable to effect the silane-silica reaction before vulcanization. This can be done by heating a rubber compounded with silica and azosilane (but not including a complete vulcanizing system).

The amount of azosilane used is similar to the amounts of prior art agents and depends on the relative amounts of silica and rubber and the method of compounding. Generally, where the rubber is pre-treated the amount of azosilane will be from 0.1 to 10, preferably 0.5 to 2, parts by weight per hundred parts of rubber (pphr). Where the azosilane is added immediately before, with, or after the silica is added to the rubber, the amount is generally from 0.2 to 20, preferably 2 to 4, parts by weight per hundred parts of silica. Preferably in the compounded rubber the amount satisfies the criteria based on rubber and on silica. These amounts relate specifically to the quantities of silica generally compounded with rubber, i.e. from 40 to 70 pphr. Where the silica is used at lower levels of compounding, or in combination with other fillers other amounts of azosilane may be preferred although it is believed that such preferred amounts will not be less than the minimum levels indicated above.

The rubber and silica or their pre-treated or modified forms may be mixed together by conventional mixing processes, e.g. on a mill or preferably in an internal mixer. As has been indicated above, other conventional compounding ingredients, e.g. other fillers, activators, accelerators, vulcanizing agents, antioxidants, antiozonants and other antidegradants and other additives, can be included during compounding, as appropriate, before, during or after compounding with silica. However, when certain antioxidants or antiozonants, such as paraphenylenediamines, are included in the formulation it may be preferable to add them after the azosilane has been mixed with the rubber and silica in order to avoid interaction between the antioxidant or antiozonant and unreacted azosilane. Such compounded silicarubber mixes may be processed and vulcanized by any of the usual means known to the art. The resulting vulcanizates have properties which are superior to those obtained without the use of coupling agents, and which are better than those obtained using the prior art coupling agents.

The coupling agents which have previously been used depend at least partly on the reactions occurring during vulcanization to become chemically bound to the rubber. This means that the prior art coupling agents are limited in their applicability especially as between different vulcanizing systems. Thus, of the prior art coupling agents set out above only the mercapto- and amino-silanes are at all effective in sulphur vulcanizing systems. Because the azosilanes of the present invention are intrinsically reactive towards olefinically unsaturated rubbers they do not depend on the vulcanizing system for their coupling action and we have had no difficulty in obtaining satisfactory results in conjunction with sulphur and peroxide vulcanizing systems.

The azosilanes of the invention are effective with olefinically unsaturated rubbers and elastomers. We have obtained good results with natural rubber (NR), synthetic cis-polyisoprene rubber, butadiene rubber (BR), styrene-butadiene rubber (SBR), trans-polypentenamer rubber, e.g. trans-polyisoprene rubber, and blends of such rubbers.

The use of the azosilanes of the invention in silica reinforced rubber can provide advantages in the physical properties of the vulcanized rubber as well as the processing advantages discussed above. Thus, silica reinforced vulcanizates having improved modulus, resilience, abrasion resistance and resistance to heat build-up can be produced. The beneficial effects of the use of azosilanes are not restricted to where silica is the only reinforcing filler. In particular, they are useful where silica and carbon black are used in combination.

The invention will be illustrated by the following Examples in which Examples 1 to 6 illustrate the synthesis of the azosilanes of the invention and Examples 7 to 21 illustrate the use of the azosilanes in producing reinforced rubber. All quantities are parts by weight unless indicated otherwise.

EXAMPLE 1

Preparation of ethyl N-p-(2-triethoxysilylethyl)phenyl carbamoylazo formate

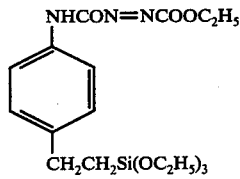

2-(Aminophenyl)ethyltriethoxysilane

A mixture of 2-(p-nitrophenyl)ethyltriethoxysilane (194 g.) and platinum oxide (0.2 g.) in absolute ethyl alcohol (500 ml) was stirred vigorously under an atmosphere of hydrogen. After 4 h. the uptake of hydrogen ceased, the ethyl alcohol was removed under reduced pressure and the residue distilled giving a colourless oil (136 g.) b.p. 140°/0.5 mm.

Analysis $C_{14}H_{23}NO_3Si$. Requires C, 59.3; H, 8.9; N, 4.9. Found C, 58.9; H, 8.8; N, 4.9%.

Phenyl-N-(2-triethoxysilylethyl)phenyl carbamate

A solution of phenyl chloroformate (9.98 g.) in light petroleum (b.p. 30°–40°, 40 ml) was added dropwise with stirring over 1.5 h. to a solution of 2-(aminophenyl)ethyltriethoxysilane (18 g.) and triethylamine (6.87 g.) in light petroleum (b.p. 30°–40° C., 60 ml). After stirring at ambient temperatures for 0.5 h. anhydrous diethyl ether (40 ml) was added and triethylamine hydrochloride removed by filtration. The filtrate was concentrated and redissolved in light petroleum (b.p. 30°–40°, 80 ml). After cooling to −20° C. the oily layer of product was separated and dried under vacuum. Yield 21.7 g. (85%).

Analysis $C_{21}H_{29}NO_5Si$. Requires C, 62.5; H,7.3; N, 3.5. Found C, 62.9; H, 7.4; N, 4.0%.

4-(2-Triethoxysilylethyl)phenyl-1-ethoxycarbonyl semicarbazide

A mixture of the above carbamate (20.7 g.), chlorotrimethylsilane (7.60 g.) and triethylamine (7.1 g.) in anhydrous toluene was refluxed for 1.5 h. After cooling the triethylamine hydrochloride was removed by filtration in an anhydrous atmosphere and the filtrate was partially concentrated to remove excess triethylamine and chlorotrimethylsilane. Ethyl carbazate (5.3 g.) was added to the filtrate and reflux maintained for 1 h. The mixture was concentrated under vacuum and the resulting oil was dissolved in a mixture of light petroleum (b.p. 40°–60°) and toluene (4:1), on cooling a white solid separated. The solid was separated by filtration and dissolved in dichloromethane. The dichloromethane solution was washed with water to remove excess ethyl carbazate. Concentration of the dichloromethane phase afforded essentially pure product, 7.60 g. (40%), m.p. 123°–124° C.

Analysis $C_{18}H_{31}N_3O_6Si$. Requires C, 52.3; H, 7.6; N, 10.2. Found C, 52.5; H, 7.7; N, 10.0%.

Ethyl-N-(2-triethoxysilyl ethyl)phenylcarbamoylazoformate (I)

The semicarbazide (9 g.) and pyridine (1.98 g.) were dissolved in dichloromethane (120 ml) and N-bromosuccinimide (4.45 g.) was added portionwise. An exothermic reaction took place and a deep red solution was formed. After stirring at ambient temperatures for 0.5 h. the dichloromethane and pyridine were removed under vacuum. A mixture of light petroleum (b.p. 30°–40° C.) and toluene 1:1 (200 ml) was added and the solids removed by filtration. The filtrate was then concentrated under vacuum to give the product as a red oil, 8 g. (90%). Infrared and nuclear magnetic resonance ($H^1$) spectra confirm its assigned structure.

EXAMPLE 2

Preparation of ethyl-N-p-(2-trimethoxysilylethyl)phenyl carbamoylazo formate

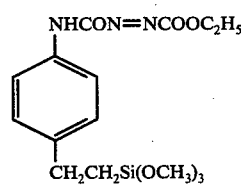

This azosilane was prepared in a manner similar to the azosilane given in Example 1. 2-(p-Nitrophenyl)ethyl trimethoxysilane was catalytically reduced in methyl alcohol giving 2-(aminophenyl)ethyl trimethoxysilane.

Analysis $C_{18}H_{23}NO_5Si$. Requires C, 59.8; H, 6.4; N, 3.9. Found C, 59.2; H, 6.4; N, 3.9%.

The aminosilane was then used to synthesise II, which was obtained as a red oil. Infrared and nuclear magnetic resonance ($H^1$) spectra confirmed the assigned structure.

EXAMPLE 3

Preparation of ethyl-N-(3-triethoxysilylpropyl)carbamoylazoformate $(C_2H_5O)_3Si(CH_2)_3NHCON=NCOOC_2H_5$ 4-(3-Triethoxysilylpropyl)-1-ethoxycarbonyl semicarbazide 3-Aminopropyltriethoxysilane (442 g.), light petroleum (b.p. 30°–40°, 1600 ml) and anhydrous triethylamine (255 g.) were placed under dry nitrogen in a three-necked flask equipped with a stirrer and dropping funnel. The mixture was cooled to −10° C. and a solution of redistilled ethyl chloroformate (217 g.) in light petroleum (b.p. 30°–40° C., 600 ml) was added dropwise over 2 h. The mixture was allowed to warm to ambient temperature and left overnight. The mixture was then rapidly filtered and the solid washed with light petroleum (2 × 300 ml). The combined filtrate was then concentrated and fractionally distilled to give ethyl-N-(3-triethoxysilylpropyl)carbamate (517 g.), b.p. 125°–135° C./0.09 mm.

The carbamate (517 g.), anhydrous triethylamine (232 g.) and dry toluene (2000 ml) were placed under dry nitrogen and warmed to 60° C. Chlorotrimethylsilane (298 g.) was then added dropwise over 0.5 h. After addition the mixture was heated under reflux for 2.5 h, cooled and filtered under nitrogen. The solid was washed with light petroleum (b.p. 30°–40° C., 100 ml) and the combined filtrate was concentrated under vacuum and fractionally distilled. The major fraction (310 g.) distilling at 80°–140° C./1 mm. This fraction was then added dropwise to a solution of ethyl carbazate in dry toluene (1000 ml) at 60° C., under nitrogen. An exothermic reaction took place and after the addition the mixture was refluxed for 1 h. The products were then concentrated under vacuum to give a pale yellow viscous oil which was recrystallized from light petroleum (b.p. 30°–40° C., 200 ml) at −20° C. The white crystalline solid was removed by filtration, washd with water and dried under vacuum to give the semicarbazide, 175 g. The infrared and nuclear magnetic resonance ($H^1$) spectra confirm the assigned structure.

Analysis $C_{13}H_{29}N_3O_6S$. Requires C, 44.4; H, 8.3; N, 11.9. Found C, 45.9; H, 8.3; N, 11.9%.

Ethyl-N-(3-triethoxysilylpropyl)carbamoylazoformate

To a solution of the semicarbazide (70 g.) and pyridine (17.4 g.) in dichloromethane (700 ml) was added N-bromosuccinimide (39.2 g.) portionwise. An organic solution was produced which was stirred for a further 2 h. after addition. The solvent and pyridine were removed under vacuum and a mixture of light petroleum (b.p. 30°–40° C., 700 ml) and dry diethyl ether (350 ml) was added. Solids were removed by filtration and washed with a further 200 ml of the solvent mixture. The combined filtrate was then concentrated under vacuum to give the product as an orange-red mobile liquid (67 g.). Infrared and nuclear magnetic resonance ($H^1$) spectra confirm the assigned structure.

Analysis $C_{13}H_{27}N_3O_6Si$. Requires C, 44.7; H, 7.8; N, 12.0. Found C, 44.0; H, 7.6; N, 12.4%.

EXAMPLE 4

Preparation of methyl-N-(3-triethoxysilylpropyl)carbamoylazoformate $(C_2H_5O)_3Si(CH_2)_3NHCON=NCOOCH_3$ The synthesis of this azo silane was achieved using the procedure of Example 3 and replacing the ethyl carbazate with methyl carbazate. The product was obtained as a red oil. Infrared and nuclear magnetic resonance ($H^1$) spectrum confirmed the assigned structure.

EXAMPLE 5

Preparation of ethyl-N-(3-trimethoxysilylpropyl)carbamoylazoformate $(CH_3)_3Si(CH_2)_3NHCON=NCOOC_2H_5$ The synthesis of this azo silane was achieved using the procedure of Example 3 and replacing 3-aminopropyltriethoxysilane by 3-aminopropyltrimethoxysilane. The product was obtained as a red oil. Infrared and nuclear magnetic resonance ($H^1$) spectra confirmed the assigned structure.

EXAMPLE 6

Preparation of ethyl-N-(3-tri-n-butoxysilylpropyl)carbamoylazoformate $(n-C_4H_9O)_3Si(CH_2)_3NHCON=NCOOC_2H_5$ The synthesis of this azo silane was achieved using the procedure of Example 3 and replacing 3-aminopropyltriethoxysilane by 3-aminopropyltributoxysilane. The product was obtained as a red oil. Infrared and nuclear magnetic resonance ($H^1$) spectra confirmed the assigned structure.

In Examples 7 to 21 following, various abbreviations are used and the following list is designed to explain the abbreviations.

| Compounds and Materials | |
|---|---|
| NR | natural rubber |
| SBR | styrene-butadiene rubber |
| BR | butadiene rubber |
| CBS | N-cyclohexyl-benzothiazole-2-sulphenamide |
| Sulfasan R | di-morpholino-disulphide (Monsanto) |
| DPG | diphenylguanidine |
| DOTG | di-o-tolyguanidine |
| MBTS | dibenzthiazyldisulphide |
| TMTD | tetramethyl thiuram disulphide |
| Santocure NS | N-tert-butylbenzothiazole-2-sulphenamide (Monsanto) |
| Santocure MOR | 2-morpholinothio-benzothiazole (Monsanto) |
| Nonox ZA | N-isopropyl-N-phenylparaphenylenediamine (ICI) |
| Flectol H | poly-2,2,4-trimethyl-1,2-dihydroquinoline |
| MB | Mercaptobenzimidazole |
| Antioxidant 2246 | 2,2'-methylene-bis(4-methyl-6-tert. butylphenol) |
| Europrene-cis (BR) | polybutadiene rubber (Anic) |
| SBR 1502 | styrene-butadiene rubber (ISR) |
| Natsyn 2200 | synthetic cis-1,4-polyisoprene (Goodyear) |
| DICUP | dicumyl peroxide (Hercules Inc.) |
| SMR5 | Standard Malaysian Rubber Grade 5 |
| SMR5L | Standard Malaysian Rubber Grade 5L |
| SRF | Semi-Reinforcing Furnace carbon black |
| HAF | High Abrasian Furnace carbon black |
| Devolite Clay | China clay (English China Clays Ltd.) |

The products of Examples 1 to 6 are referred to as azosilanes 1 to 6 for convenience.

Conditions and Tests

All the vulcanizates are cured to $t_c95$, i.e. to 95% of the torque difference as obtained from Monsanto rheometer traces.

| | | | |
|---|---|---|---|
| M 100 | | 100% | |
| M 200 | Modulus at | 200% | extension (Mega Pascals) |
| M 300 | | 300% | |
| MR100 | Relaxed Modulus 100 (i.e. M100 measured after 1 minute under 100% extension) | | |
| T.S. | Tensile Strength | | |
| E.B. | Extension to Break | | |

The Mooney Scorch Time, Compression Set, Dunlop Resilience, and Akron Abrasion are all measured per BS903 (relevant conditions stated).

The Goodrich heat build-up is measured per ASTM D623 under the following conditions: Initial Temperature of sample 23° C., Frequency 25 Hz, Stroke 0.2 inch (5 mm), static stress 159.8 p.s.i. (11.24 kg cm$^{-2}$), time 30 minutes: the result is quoted as a rise in temperature (Δ° C.).

EXAMPLE 7

The azo silanes, synthesised in Examples 1 and 2, were compared to the use of 3-mercaptopropyltrimethoxysilane (Union Carbide, A189), in natural rubber (NR) formulations including silica as filler, Hi-Sil 233 (PPG Industries, Inc.).

It is clear from the data shown in Table I that both the azo silanes I and II are giving promoting effect, which is comparable to the commercially available reagent A189.

TABLE I

| | | | | | | | | | | |
|---|---|---|---|---|---|---|---|---|---|---|
| SMR 5 | 100 | 100 | 100 | 100 | 100 | 100 | 100 | 100 | 100 | 100 |
| Hi-Sil 233 | 50 | 50 | 50 | 50 | 50 | 50 | 50 | 50 | 50 | 50 |
| Zinc Oxide | 7.5 | 7.5 | 7.5 | 7.5 | 7.5 | 7.5 | 7.5 | 7.5 | 7.5 | 7.5 |
| Stearic acid | 3 | 3 | 3 | 3 | 3 | 3 | 3 | 3 | 3 | 3 |
| Sulphur | 3.65 | 3.65 | 3.65 | 3.65 | 3.65 | 3.65 | 3.65 | 3.65 | 3.65 | 3.65 |
| CBS | 0.69 | 0.9 | 0.9 | 0.9 | 0.9 | 0.9 | 0.9 | 0.9 | 0.9 | 0.9 |
| TMTD | 0.4 | 0.4 | 0.4 | 0.4 | 0.4 | 0.4 | 0.4 | 0.4 | 0.4 | 0.4 |
| A189 | — | 0.75 | 1.5 | 3.0 | — | — | — | — | — | — |
| Azo silane 1 | — | — | — | — | 0.75 | 1.5 | 3.0 | — | — | — |
| Azo silane 2 | — | — | — | — | — | — | — | 0.4 | 1.0 | 2.0 |
| Cure time at 140° C (min) | 18 | 14 | 9 | 7 | 17 | 15 | 12 | 13 | 12 | 11 |
| M300 (MPa) | 3.05 | 11.0 | 15.2 | 16.3 | 6.73 | 9.58 | 18.0 | 7.77 | 11.3 | 19.3 |
| T.S. (MPa) | 15.6 | 29.9 | 29.9 | 32.9 | 22.0 | 27.0 | 27.1 | 27.3 | 27.2 | 23.1 |
| E.B. % | 684 | 596 | 511 | 535 | 623 | 603 | 412 | 671 | 550 | 341 |

EXAMPLE 8

In this case the azo silanes synthesised in Examples 3 to 6 are compared to the use of A189 in natural rubber formulation containing, Hi-Sil 233.

TABLE II

| | | | | | | |
|---|---|---|---|---|---|---|
| SMR 5 | 100 | 100 | 100 | 100 | 100 | 100 |
| Hi-Sil 233 | 50 | 50 | 50 | 50 | 50 | 50 |
| Zinc oxide | 5 | 5 | 5 | 5 | 5 | 5 |
| Stearic acid | 3 | 3 | 3 | 3 | 3 | 3 |
| Sulphur | 2.5 | 2.5 | 2.5 | 2.5 | 2.5 | 2.5 |
| MBTS | 1.5 | 1.5 | 1.5 | 1.5 | 1.5 | 1.5 |
| DPG | 1.2 | 1.2 | 1.2 | 1.2 | 1.2 | 1.2 |
| A189 | 13 | 2.0 | — | — | — | — |
| Azo silane 3 | — | — | 2.0 | — | — | — |
| Azo silane 4 | — | — | — | 2.0 | — | — |
| Azo silane 5 | — | — | — | — | 2.0 | — |
| Azo silane 6 | — | — | — | — | — | 2.0 |
| Cure time 140° C (min) | 18 | 11 | 16 | 15 | 14 | 18 |
| M300(MPa) | 7.57 | 16.2 | 19.9 | 21.2 | 11.0 | 11.8 |
| T.S. (MPa) | 30.8 | 29.1 | 32.0 | 28.0 | 31.5 | 32.1 |

TABLE II-continued

| | | | | | | |
|---|---|---|---|---|---|---|
| E.B. % | 634 | 454 | 437 | 369 | 576 | 568 |

In all cases there is an enhancement of properties and the azo silanes 3 to 6 are behaving as silane coupling agents.

EXAMPLE 9

In Examples 7 and 8 the sequence of addition was:
(1) Addition of silane to a masterbatch of SMR5 and Hi-Sil 233
(2) Compounding ingredients The results shown in this example demonstrate the effect on properties by two different modes of addition of the silane.

TABLE III

| | A | B | A | B |
|---|---|---|---|---|
| SMR5 | 100 | 100 | 100 | 100 |
| Hi-Sil 233 | 50 | 50 | 50 | 50 |
| Zinc oxide | 7.5 | 7.5 | 7.5 | 7.5 |
| Stearic acid | 3 | 3 | 3 | 3 |
| Sulphur | 3.75 | 3.75 | 3.75 | 3.75 |
| CBS | 0.9 | 0.9 | 0.9 | 0.9 |
| TMTD | 0.4 | 0.4 | 0.4 | 0.4 |
| A189 | 1.0 | 1.0 | — | — |
| Azo silane 1 | — | — | 1.0 | 1.0 |
| M100 (MPa) | 1.76 | 0.45 | 1.68 | 2.11 |
| M300 (MPa) | 7.91 | 1.84 | 10.8 | 12.5 |
| T.S. (MPa) | 23.0 | 5.57 | 24.1 | 27.7 |
| E.B. % | 581 | 574 | 497 | 543 |
| Cure time at 140° C (min) | 9 | 15 | 11 | 11 |

Table III shows the results, samples A involved the sequence of addition:
(i) Addition of silane to a masterbatch of SMR5 and Hi-Sil 233
(ii) Compounding ingredients Samples B involved the sequence of addition:
(i) Compounding ingredients added to a masterbatch of SMR5 and Hi-Sil 233
(ii) Silane.

It is clear from the results that there is a dramatic reduction in properties with A189 when mode of addition B is used. In the case of the azo silane 3, there is no reduction in properties.

In the following examples mode of addition A was used.

EXAMPLE 10

This example shows the effect of the silanes, A189 and azo silane 3 (prepared in Example 3) on the Mooney Scorch time measured at 120° C.

Table IV shows the results using the two silanes in different vulcanization systems, a sulphurless system (Santocure NS/Sulfasan R) and a sulphur system (S/MBTS). It is clear that use of A189 causes a dramatic decrease in the scorch time, whereas the azo silane has virtually no effect on the scorch time.

TABLE IV

| | | | | | | |
|---|---|---|---|---|---|---|
| SMR5 | 100 | 100 | 100 | 100 | 100 | 100 |
| Hi-Sil 233 | 50 | 50 | 50 | 50 | 50 | 50 |
| Zinc oxide | 5 | 5 | 5 | 5 | 5 | 5 |
| Stearic acid | 1.5 | 1.5 | 1.5 | 3 | 3 | 3 |
| Sulphur | — | — | — | 2.5 | 2.5 | 2.5 |
| NBTS | — | — | — | 1.5 | 1.5 | 1.5 |
| Santocure NS | 1.5 | 1.5 | 1.5 | — | — | — |
| Sulfasan R | 1.5 | 1.5 | 1.5 | — | — | — |
| DPG | — | — | — | 1.2 | 1.2 | 1.2 |
| TMTD | 0.5 | 0.5 | 0.5 | — | — | — |
| A189 | — | 3.0 | — | — | 2.0 | — |
| Azo silane 3 | — | — | 3.0 | — | — | 2.0 |
| Mooney Scorch at 120°, t+5 (min) | 13.1 | 4.5 | 14.2 | 14.0 | 1.6 | 13.5 |

EXAMPLE 11

This example illustrates the use of a variety of antioxidants in the case of azo silane 3.

TABLE V

| | A | B | A | B | A | B | A | B |
|---|---|---|---|---|---|---|---|---|
| SMR5 | 100 | 100 | 100 | 100 | 100 | 100 | 100 | 100 |
| Hi-Sil 233 | 50 | 50 | 50 | 50 | 50 | 50 | 50 | 50 |
| Zinc oxide | 5 | 5 | 5 | 5 | 5 | 5 | 5 | 5 |
| Stearic acid | 3 | 3 | 3 | 3 | 3 | 3 | 3 | 3 |
| Sulphur | 2.5 | 2.5 | 2.5 | 2.5 | 2.5 | 2.5 | 2.5 | 2.5 |
| MBTS | 1.0 | 1.0 | 1.0 | 1.0 | 1.0 | 1.0 | 1.0 | 1.0 |
| DPG | 2.0 | 2.0 | 2.0 | 2.0 | 2.0 | 2.0 | 2.0 | 2.0 |
| Nonox ZA | 2.0 | 2.0 | — | — | — | — | — | — |
| Antioxidant 2246 | — | — | 2.0 | 2.0 | — | — | — | — |
| Flectol H | — | — | — | — | 2.0 | 2.0 | — | — |
| MB | — | — | — | — | — | — | 2.0 | 2.0 |
| Azo silane 3 | 1.2 | 1.2 | 1.2 | 1.2 | 1.2 | 1.2 | 1.2 | 1.2 |
| M300 (MPa) | 9.60 | 18.6 | 20.5 | 18.5 | 21.5 | 19.0 | 9.98 | 18.9 |
| T.S. (MPa) | 33.3 | 33.9 | 33.7 | 32.2 | 31.0 | 33.8 | 31.8 | 32.7 |
| E.B. % | 628 | 475 | 448 | 463 | 403 | 476 | 612 | 475 |
| Cure time at 140° C (min) | 15 | 14 | 15 | 14 | 15 | 14 | 19 | 17 |

In Samples A, the sequence of addition of the various ingredients was as follows:

(i) Antioxidant added to a masterbatch of SMR5 and Hi-Sil 233
(ii) Addition of azo silane 3
(iii) Addition of reamining ingredients.

For Samples B, the sequence of addition of the various ingredients was as follows:

(i) Addition of azo silane 3 to a masterbatch of SMR5 and Hi-Sil 233
(ii) Addition of compounding ingredients
(iii) Addition of antioxidant For antioxidants 2246 and Flectol H, the mode of addition is unimportant. Nonox ZA and MB the antioxidant must be added at the end of the mixing cycle (Samples B), addition before the azo silane 3 (Samples A) renders the coupling agent inactive.

Antiozonants are generally of the phenylenediamine type and should therefore be added following the procedure for Sample B, i.e. at the end of the mixing cycle.

EXAMPLE 12

The preparation of a masterbatch of SMR5, Hi-Sil 233 is possible, the azo silane being added to an internal mixer.

Table VI gives data for two different modes of addition of the azo silane 3 in a Banbury mixing cycle.

| | Time (min) | |
|---|---|---|
| mixing cycle 1 :- | | |
| i) SMR5 (500 g.) + azo silane 3 (6.0 g.) added | — | |
| ii) ½ Hi-Sil 233 (125 g.) | 1.5 | Masterbatch A |
| iii) ½ Hi-Sil 233 (125 g.) | 3 | |
| iv) Dump | 4.5 | |
| Mixing cycle 2 :- | | |
| i) SMR5 added (500 g.) | — | |
| ii) ½ Hi-Sil 233 (125 g.) | 1.5 | Masterbatch B |
| iii) ½ Hi-Sil 233 (125 g.) + azo silane 3 (6.0 g.) | 3 | |
| iv) Dump | 4.5 | |
| A control with no azo silane 3 was also produced | | Masterbatch C |

TABLE VI

| | | | |
|---|---|---|---|
| Masterbatch A | 151.2 | — | — |
| Masterbatch B | — | 151.2 | — |
| Masterbatch C | — | — | 150 |
| Zinc oxide | 5 | 5 | 5 |
| Stearic acid | 3 | 3 | 3 |
| Sulphur | 2.5 | 2.5 | 2.5 |
| MBTS | 1.0 | 1.0 | 1.0 |
| DPG | 2.0 | 2.0 | 2.0 |
| M300 (MPa) | 16.2 | 15.4 | 8.0 |
| Cure time at 140° C (min) | 15 | 14 | 16 |

The mode of addition of the azo silane is unimportant as shown by the data in Table VI.

EXAMPLE 13

This example illustrates the use of clay instead of silica. Table VII gives data for a compound involving the use of Devolite Clay.

TABLE VII

| | | | |
|---|---|---|---|
| SMR5L | 100 | 100 | 100 |
| Devolite Clay | 50 | 50 | 50 |
| Zinc oxide | 2.5 | 2.5 | 2.5 |
| Stearic acid | 1.0 | 1.0 | 1.0 |
| Sulphur | 1.25 | 1.25 | 1.25 |
| Santocur MOR | 0.5 | 0.5 | 0.5 |
| TMTD | 0.1 | 0.1 | 0.1 |
| A189 | — | 1.7 | — |
| Azo silane 3 | — | — | 1.7 |
| M300 (MPa) | 3.72 | 5.46 | 6.65 |
| T.S. (MPa) | 22.2 | 17.4 | 16.3 |
| E.B. % | 658 | 548 | 550 |
| Cure time at 140° C (min) | 20 | 10 | 22 |

The azo silane is therefore as effective as the commercial reagent A189 in formulations involving the use of devolite clay.

EXAMPLE 14

Table VIII shows the data for a comparative study of a variety of properties between azo silane 3 and A189.

TABLE VIII

| | | | | | | | |
|---|---|---|---|---|---|---|---|
| SMR5 | 100 | 100 | 100 | 100 | 100 | 100 | 100 |
| Hi-Sil 233 | 50 | 50 | 50 | 50 | 50 | 50 | 50 |
| Stearic acid | 3 | 3 | 3 | 3 | 3 | 3 | 3 |
| Sulphur | 2.5 | 2.5 | 2.5 | 2.5 | 2.5 | 2.5 | 2.5 |
| MBTS | 1.5 | 1.5 | 1.5 | 1.5 | 1.5 | 1.5 | 1.5 |
| DPG | 1.2 | 1.2 | 1.2 | 1.2 | 1.2 | 1.2 | 1.2 |
| Antioxidant 2246 | 2.0 | 2.0 | 2.0 | 2.0 | 2.0 | 2.0 | 2.0 |
| A189 | — | 1.3 | 2.0 | 3.0 | — | — | — |
| Azo silane 3 | — | — | — | — | 1.3 | 2.0 | 3.0 |
| M300 (MPa) | 6.54 | 13.9 | 14.4 | 4.57 | 20.3 | 24.5 | — |
| T.S. (MPa) | 30.4 | 33.9 | 33.1 | 19.1 | 30.2 | 27.9 | 19.4 |
| E.B. % | 701 | 555 | 553 | 659 | 417 | 334 | 261 |
| Compression set % | 67 | 25 | 27 | 59 | 34 | 24 | 24 |
| Resilience (Dunlop) % | 72.5 | 81.7 | 78.3 | 78.9 | 87.0 | 86.0 | 88.8 |
| Goodrich Heat build-up, temp. rise (Δ° C) | 23 | 16 | 17 | 14 | 13 | 11 | 12 |
| Akron abrasion (wt.loss/500 rev.) | 96 | 54 | 55 | 129 | 27 | 23 | 16 |
| Cure time at 140° C (min) | 16 | 14 | 10 | 18 | 14 | 15 | 15 |

Several notable points can be made from the comparison in Table VIII.

(1) For equivalent amounts there is a superior improvement in resilience in using azo silane 3 as compared to A189, and this effect leads to an improvement in the heat build-up data.

(2) Abrasion resistance (Akron abrasion test) is significantly improved when using azo silane 3, as compared to A189.

(3) At high levels of A189 (3 pphr) there is a dramatic reduction in physical properties. (M300, E.B., compression set, and abrasion) whereas with azo silane 3 the improvement continues except in the case of tensile strength.

EXAMPLE 15

This example illustrates the use of azo silane 3 with SBR 1502 (styrene-butadiene rubber), and compared with A189.

As with NR, azo silane 3 shows a significant improvement over A189.

TABLE IX

| | | | | | |
|---|---|---|---|---|---|
| SBR 1502 | 100 | 100 | 100 | 100 | 100 |
| Hi-Sil 233 | 50 | 50 | 50 | 50 | 50 |
| Zinc oxide | 4.0 | 4.0 | 4.0 | 4.0 | 4.0 |
| Stearic acid | 1.0 | 1.0 | 1.0 | 1.0 | 1.0 |
| Sulphur | 2.5 | 2.5 | 2.5 | 2.5 | 2.5 |
| MBTS | 1.0 | 1.0 | 1.0 | 1.0 | 1.0 |
| DOTG | 1.0 | 1.0 | 1.0 | 1.0 | 1.0 |
| A189 | — | 1.0 | 2.0 | — | — |
| Azo silane 3 | — | — | — | 1.0 | 2.0 |
| Mooney Scorch at 120° C, t+5 (min) | 52.5 | 16.6 | 2.6 | 37.2 | 27.5 |
| Cure time at 140° C (min) | 38 | 23 | 18 | 27 | 38 |
| MR100 | 1.53 | 2.2 | 2.6 | 2.5 | 2.7 |
| M300 | 6.29 | 13.8 | — | 16.7 | — |
| T.S. | 15.4 | 22.9 | 23.2 | 23.1 | 18.9 |
| E.B. | 508 | 421 | 339 | 370 | 283 |
| Resilience % | 67.2 | 67.8 | 68.2 | 72.5 | 73.1 |
| Compression set % | 25 | 20 | 19 | 17 | 17 |
| Akron Abrasion (wt.loss/500 rev.) | 90 | 44 | 33 | 33 | 23 |

EXAMPLE 16

This example illustrates the use of azo silane 3 with butadiene rubber (BR) using Europrene-cis (Anic, Italy).

TABLE X

| | | |
|---|---|---|
| European-cis | 100 | 100 |
| Hi-Sil 233 | 50 | 50 |
| Zinc oxide | 5 | 5 |
| Stearic acid | 3 | 3 |
| Sulphur | 2.5 | 2.5 |
| MBTS | 1.5 | 1.5 |
| DPG | 1.2 | 1.2 |
| Azo silane 3 | — | 2.0 |
| MR100 | 1.804 | 3.38 |
| M200 | 3.87 | 9.07 |
| Cure time at 155° C (min) | 26 | 15 |

Azo silane is therefore effective when using BR.

EXAMPLE 17

A blend of NR/BR, 80/20 was used with azo silane 3 and Table XI shows the results. Azo silane 3 is effective when used in this blend.

TABLE XI

| | | |
|---|---|---|
| SMR5 | 80 | 80 |
| Europrene-cis | 20 | 20 |
| Hi-Sil 233 | 50 | 50 |
| Zinc oxide | 5 | 5 |
| Stearic acid | 3 | 3 |
| Sulphur | 2.5 | 2.5 |
| MBTS | 1.5 | 1.5 |
| DPG | 1.2 | 1.2 |
| Azo silane 3 | — | 2.0 |
| MR100 (MPa) | 1.32 | 2.68 |
| M200(MPa) | 3.18 | 9.38 |
| Cure time at 145° C (min) | 21 | 11 |

EXAMPLE 18

The azo silane 3 was used in a formulation which contained a synthetic cis-polyisoprene (Natsyn 2200).

Table XII gives the results and shows the enhancement in properties with the incorporation of azo silane 3.

TABLE XII

| | | | |
|---|---|---|---|
| Natsyn 2200 | 100 | 100 | 100 |
| Hi-Sil 233 | 50 | 50 | 50 |
| Zinc oxide | 5 | 5 | 5 |
| Stearic acid | 2.5 | 2.5 | 2.5 |
| Sulphur | 2.5 | 2.5 | 2.5 |
| MBTS | 1.0 | 1.0 | 1.0 |
| DPG | 2.0 | 2.0 | 2.0 |
| Azo silane 3 | — | 0.25 | 0.5 |
| Cure time at 140° C (min) | 30 | 30 | 22 |
| MR100 (MPa) | 1.836 | 2.188 | 2.74 |
| M300 (MPa) | 6.52 | 13.2 | 21.0 |
| T.S. (MPa) | 26.7 | 27.8 | 25.2 |
| E.B.% | 691 | 557 | 364 |

EXAMPLE 19

Many applications of silane coupling agents involve the use of these reagents in a mixed filler system, carbon black/silica, i.e. a portion of the carbon black is replaced by silica. Table XIII shows the data for a study of a carbon black/silica mixed system, using A189 and azo silane 3 with carbon black (SRF Semi-reinforcing furnace) in which the initial carbon black level is 60 pphr and 10 pphr are replaced by 15 pphr of Hi-Sil 233.

TABLE XIII

| | | | | |
|---|---|---|---|---|
| SMR5L | 100 | 100 | 100 | 100 |
| SRF | 60 | 50 | 50 | 50 |
| Hi-Sil 233 | — | 15 | 15 | 15 |
| Dutrex R | 5 | 5 | 5 | 5 |
| Flectol H | 2 | 2 | 2 | 2 |
| Zinc oxide | 5 | 5 | 5 | 5 |
| Stearic acid | 3 | 3 | 3 | 3 |
| Sulphur | 2.5 | 2.5 | 2.5 | 2.5 |
| CBS | 0.6 | 0.6 | 0.6 | 0.6 |
| Azo silane 3 | — | — | 0.6 | — |
| A189 | — | — | — | 0.6 |
| Cure time at 140° C (min) | 35 | 45 | 45 | 31 |
| MR100 (MPa) | 1.94 | 1.35 | 1.68 | 1.46 |
| M300 (MPa) | 12.4 | 9.41 | 11.2 | 9.62 |
| T.S. (MPa) | 24.0 | 24.5 | 22.3 | 24.5 |
| E.B. % | 491 | 578 | 487 | 553 |
| Resilience (Dunlop) % | 76 | 73 | 74 | 73 |
| Tear strength Die C (N) | 44.4 | 53.7 | 59.0 | 102.8 |
| Goodrich Heat build-up, (Δ° C) | 23 | 24.5 | 21.5 | 24.5 |
| Akron Abrasion (wt. loss (mg)/500 rev.) | 86 | 83 | 40 | 60 |

Table XIV gives data for a similar comparison but using a High-Abrasion Furnace (HAF) carbon black.

TABLE XIV

| | | | | |
|---|---|---|---|---|
| SMR5L | 100 | 100 | 100 | 100 |
| HAF | 60 | 50 | 50 | 50 |
| Hi-Sil 233 | — | 15 | 15 | 15 |
| Dutrex R | 5 | 5 | 5 | 5 |
| Flectol H | 2 | 2 | 2 | 2 |
| Zinc oxide | 5 | 5 | 5 | 5 |
| Stearic acid | 3 | 3 | 3 | 3 |
| Sulphur | 2.5 | 2.5 | 2.5 | 2.5 |
| CBS | 0.6 | 0.6 | 0.6 | 0.6 |
| Azo silane 3 | — | — | 0.6 | — |
| A189 | — | — | — | 0.6 |
| Cure time at 140° C (min) | 39 | 48 | 43 | 27 |
| MR100 (MPa) | 2.38 | 1.80 | 2.06 | 2.06 |
| M300 (MPa) | 17.4 | 12.8 | 15.3 | 14.8 |
| T.S. (MPa) | 27.6 | 27.3 | 27.6 | 27.4 |
| E.B. % | 447 | 511 | 479 | 487 |
| Resilience (Dunlop) % | 64 | 60 | 60 | 60 |
| Tear strength Die 'c', (N) | 87 | 101 | 99 | 96 |
| Goodrich heat build-up, (Δ° C) | 32 | 35.5 | 32 | 35 |
| Akron Abrasion (wt.loss (mg)/500 rev.) | 33 | 41 | 32 | 34 |

The results in Tables XIII and XIV indicate that the azo silane 3 is effective when both types of carbon black are used in conjunction with Hi-Sil 233, whereas A189 only appears to be effective in the case of the HAF carbon black. A portion of the carbon black is replaced by silica to improve properties such as tear and chipping, and mixed filler systems find applications in the off-the-road tyres, e.g. earthmoving vehicle tyres. Using azo silane 3 the good tear-strength properties obtained by addition of silica are maintained and there is a significant improvement in other properties (M300, heat build-up, abrasion resistance).

EXAMPLE 20

In Examples 7 to 19, modification was carried out on the dry polymer, either by mixing on a mill or in an internal mixer. With the azo silanes modification of the polymer can be carried out in solution, and this example illustrates the modification of natural rubber in solution with azo silane 3 and use of the modified rubber in conjunction with Hi-Sil 233 added to the dry rubber on a mill.

Deproteinised natural rubber (DPNR) (50 g.) was dissolved in dichloromethane (1000 ml) and azo silane 3 (1 g.) added. After 2 days at ambient temperatures the red colour due to the azo silane 3 had been discharged and the modified rubber was isolated by precipitation with methyl alcohol, dried in vacuo. The following ingredients were then added in a mill to the modified rubber (51 g.):

| | | |
|---|---|---|
| Hi-Sil 233 | 25 | g. |
| Zinc oxide | 1.7 | g. |
| Stearic acid | 1 | g. |
| Sulphur | 0.85 | g. |
| MBTS | 0.5 | g. |
| DPG | 0.4 | g. |

A sample of DPNR was cured in a similar way but in the absence of azo silane 3.

Both samples were cured for 60 min. at 145° C.

| | Control | Modified DPNR |
|---|---|---|
| M300 (MPa) | 1.84 | 3.75 |
| E.B. % | 679 | 409 |

The above results show that the azo silane 3 is effective in improving properties when the modification is carried out in solution.

EXAMPLE 21

In Examples 7 to 20, sulphur vulcanizates have been used. However, azo silane 3 is effective when using a peroxide curing system as shown in Table XV. Samples were cured for 10 mins. at 100° C. and then 50 mins. at 150° C.

TABLE XV

| | | | | |
|---|---|---|---|---|
| SMR5 | 100 | 100 | 100 | 100 |
| Hi-Sil 233 | 50 | 50 | 50 | 50 |
| Dicup | 1.0 | 1.0 | 1.0 | 1.0 |
| Azo silane 3 | — | 1.0 | 2.0 | 3.0 |
| MR100 (MPa) | 1.38 | 1.164 | 1.40 | 1.44 |
| M300 (MPa) | 6.49 | 7.99 | 9.35 | 10.6 |
| T.S. (MPa) | 24.0 | 20.0 | 19.8 | 19.4 |
| E.B. % | 608 | 497 | 464 | 417 |

What is claimed is:

1. A method of compounding rubber with silica which comprises including in the rubber a compound of the formula:

$$Y - X - CO - N = N - CO - X^1 - Z$$

where X and $X^1$ are the same or different and each is an imino group, an oxygen atom or a substituted or unsubstituted methylene group;

Y is a substituted or unsubstituted alkyl aryl or aralkyl group, or is the same as Z; and Z is an alkyl, aryl or aralkyl group which has as substituent at least one silane group of the formula: —Si(OR)$_3$ or —OSi(OR$_3$) in which R is a straight or branched chain alkyl group.

2. A method as claimed in claim 1 wherein R is a $C_1$ to $C_6$ alkyl group.

3. A method as claimed in claim 1 wherein said compound is of the formulae:

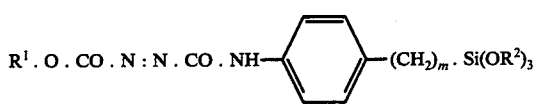

or

R$^1$.O.CO.N:N.CO.NH(CH$_2$)$_m$.Si(OR$^2$)$_3$ where R$^1$ and R$^2$ are the same or different and each is a straight or branched chain alkyl group;

m is 0, 1, 2 or 3; and n is 1, 2 or 3.

4. A method as claimed in claim 3 wherein R$^1$ and R$^2$ are C$_1$ to C$_6$ alkyl groups.

5. A method as claimed in claim 1 wherein the rubber is treated by adding the compound to the rubber prior to compounding the treated rubber with silica.

6. A method as claimed in claim 5 wherein the rubber is in the form of solid rubber or rubber solution.

7. A method as claimed in claim 1 comprising compounding silica into rubber and mixing into the rubber or compounded rubber said compound.

8. A method as claimed in claim 6 wherein subsequent to the inclusion of the compound the rubber is heated to complete reaction between the rubber and the compound.

9. A method as claimed in claim 8 wherein the compound has the formula:

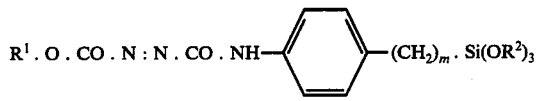

wherein R$^1$, R$^2$ are the same or different and each is a straight or branched chain alkyl group; and m is 0, 1, 2 or 3, and the temperature during heating does not exceed 100° C.

10. A method as claimed in claim 8 wherein the compound has the formula:

R$^1$.O.CO.N:N.CO.NH.(CH$_2$)$_n$.Si(OR$^2$)$_3$ where R$^1$, R$^2$ are the same or different and each is a straight or branched chain alkyl group; and m is 1, 2 or 3 and the temperature during the heating does not exceed 150° C.

11. A method as claimed in claim 6 wherein the amount of the compound is from 0.1 to 10 pphr.

12. A method as claimed in claim 6 wherein the amount of the compound is from 0.2 to 20 pph silica.

13. Rubber compounded with silica and a compound as defined in claim 6.

14. Rubber compounded with silica as claimed in claim 13 and including at least one member selected from the group consisting of fillers other than silica, activators, accellerators, vulcanizing agents, antioxidants and antiozonants.

15. A silica reinforced rubber vulcanizate made by vulcanizing rubber compounded with silica as claimed in claim 13.

* * * * *